US005750512A

United States Patent [19]
Birkmayer

[11] Patent Number: 5,750,512
[45] Date of Patent: May 12, 1998

[54] NADH AND NADPH THERAPEUTIC AGENTS FOR NASAL, SUBLINGUAL, RECTAL AND DERMAL ADMINISTRATION

[75] Inventor: Joerg G. D. Birkmayer, Vienna, Austria

[73] Assignee: Birkmayer Pharmaceuticals, Inc., New York, N.Y.

[21] Appl. No.: 673,407

[22] Filed: Jul. 11, 1996

Related U.S. Application Data

[63] Continuation of Ser. No. 373,147, Jan. 17, 1995, abandoned.

[51] Int. Cl.$^6$ .................................................. A61K 31/70
[52] U.S. Cl. ................................................................ 514/52
[58] Field of Search ........................................... 514/52

[56] References Cited

U.S. PATENT DOCUMENTS

| | | | |
|---|---|---|---|
| 4,970,200 | 11/1990 | Birkmayer et al. | 514/52 |
| 5,019,561 | 5/1991 | Birkmayer | 514/52 |
| 5,332,727 | 7/1994 | Birkmayer | 514/52 |

FOREIGN PATENT DOCUMENTS

| | | |
|---|---|---|
| 2135203 | 12/1993 | Canada . |
| 2057456 | 7/1996 | Canada . |
| 0 256 472 | 2/1988 | European Pat. Off. . |
| 0 496 479 B1 | 7/1992 | European Pat. Off. . |
| 0 615 747 | 9/1994 | European Pat. Off. . |
| 63-301810 | 12/1988 | Japan . |
| 92/0275 | 12/1992 | South Africa . |
| WO 91/07947 | 6/1991 | WIPO . |
| WO 93/24107 | 12/1993 | WIPO . |

OTHER PUBLICATIONS

Corbisier, P. et al., "Involvement of mitochondria in cell degeneration", *European Journal of Cell Biology*, vol. 51 (1990), pp. 173–182.

Primary Examiner—Theodore J. Criares
Attorney, Agent, or Firm—Kenyon & Kenyon

[57] ABSTRACT

NADH and/or NADPH is applied topically to the skin. It was surprising and totally unexpected to discover that NADH and NADPH are absorbed by the skin and penetrate the cutis to be taken up by the skin cells, where they stimulate certain enzymes which are essential for the energy production of the cells. The enzymes stimulated are principally the mitochondrial enzymes. The NADH and/or NADPH can be incorporated into a skin compatible cream, lotion or cosmetic. Liposomes are ideal vesicles for carrying the NADH and/or NADPH into the skin. In other embodiments of the invention, NADH and/or NADPH is administered nasally (e.g., as a liquid spray or a powder spray through the nostrils), sublingually (e.g., in the form of uncoated tablets inserted underneath the tongue) and rectally (e.g., in the form of suppositories) for known therapeutic effects; e.g., the treatment of Parkinson's disease Alzheimer's Disease and depression.

7 Claims, No Drawings

NADH AND NADPH THERAPEUTIC AGENTS FOR NASAL, SUBLINGUAL, RECTAL AND DERMAL ADMINISTRATION

This application is a continuation of application Ser. No. 08/373,147 filed Jan. 17, 1995 now abandoned.

BACKGROUND OF THE INVENTION

1. Field of the Invention

The invention relates to the use of NADH and NADPH as therapeutic agents, and particularly to administering NADH and NADPH nasally, sublingually, rectally and topically to the skin for a variety of therapeutic effects.

2. Description of Related Art

Nicotinamide-adenine-dinucleotide in its reduced form ("NADH") and nicotinamide-adenine-phosphate-dinucleotide in its reduced form ("NADPH") are physiological substances which occur in all living cells including human cells. These substances are cofactors for a variety of enzymes, the majority of which catalyze oxidation-reduction reactions. Prior to recent discoveries as to the therapeutic properties of these compounds, their principal utility has been as diagnostic tools in clinical biochemistry and as essential components in reaction kits, for example, in measuring lactatdehydrogenase (LDH).

The most important function of NADH is its driving force for cell respiration. When using oxygen, NADH forms water and 3 ATP molecules in accordance with the following formula: $NADH + H^+ + \frac{1}{2}O_2 + 3\ Pi + 3\ ATP \rightarrow NAD^+ + 3\ ATP + 4H_2O$. Thus, with 1 NADH molecule, 3 ATP molecules are obtained which have an energy of approximately 21 kilocalories. This process is called oxidative phosphorylation. The supply of NADH and/or NADPH makes this work much easier for the organism, because it has greater energy reserves as a result.

More recently, NADH and NADPH and pharmaceutically acceptable salts thereof have been shown to be useful in the treatment of Parkinson's Disease. The effectiveness of these agents for this purpose is documented in my existing U.S. Pat. Nos. 4,970,200 and 5,019,561, the disclosures of which are incorporated herein by reference.

In addition, I have discovered that these substances are effective in the treatment of Morbus Alzheimer (i.e., Alzheimer's Disease), which is the subject of my U.S. Pat. No. 5,444,053 filed on Sep. 15, 1993, as well as in the treatment of mental depression, which is the subject of my abandoned applications Ser. Nos. 07/815,407, 07/978,034 and 08/097,988 filed on Dec. 31, 1991, Nov. 18, 1992 and Jul. 27, 1993, respectively.

Prior to my recent discoveries, NADH and NADPH have never been considered for therapeutic use, probably because it was believed that these compounds are rather unstable and, hence, not capable of being absorbed by the intestines of the human body. It would have been expected that these substances would be hydrolized in the plasma within a few seconds.

However, studies performed recently using NADH and NADPH demonstrate that these assumptions are incorrect. When NADH and NADPH were applied intravenously to patients with Parkinson's disease, a remarkable beneficial effect was observed which lasted at least 24 hours. See U.S. Pat. Nos. 4,970,200 and 5,019,561. This indicates that NADH and NADPH are not rapidly degraded in the plasma and blood.

One drawback to intravenous application of NADH and NADPH is that it requires an injection which has to be performed in a hospital or at the physician's practice. This requirement can be inconvenient or demanding on the patient's schedule. Therefore, it would be desirable to find another form for NADH and NADPH which would allow patients to take these substances regularly under their own supervision.

My U.S. Pat. No. 5,332,727 teaches a stable, ingestable and absorbable NADH and/or NADPH therapeutic composition which can be taken orally. It was discovered that this oral form is absorbed by the intestine, and is effective in the treatment of Parkinson's disease and Alzheimer's disease. However, it would also be desirable to administer NADH and NADPH in ways other than orally and intravenously for a variety of therapeutic effects.

For example, my copending application Ser. No. 08/122,035 filed on Sep. 15, 1993 teaches that NADH and NADPH are effective in the treatment of Alzheimer's disease when administered orally or intravenously. However, it would also be desirable to administer the NADH or NADPH intranasally, since nasal administration has proven to be a direct and effective way to deliver neurologic agents to the brain (see International Publication No. WO 91/07947). The olfactory neural pathway is a route for delivering neurologic agents to the brain which circumvents the bloodstream, and thereby avoids the need for the agent to traverse the blood-brain barrier.

It has also been discovered that the mitochondria play a major role in cell degeneration. Recent studies suggest that modifications of mitochondria leading to their uncoupling are harmful to cells, and are responsible for some of the degenerative processes involved in natural or externally induced cell death. It has been observed that the inactivation of mitochondria results in diminished ATP production which adversely affects cellular homeostasis, thereby leading to cell degeneration. See Corbisier, P. et al. "Involvement of Mitochondria in Cell Degeneration" in *European Journal of Cell Biology*, Vol. 51, pp. 173–182 (1990). Corbisier et al. have suggested that if the observed cellular degeneration was due to an intracellular energy decrease caused by inactivation of the mitochondria, a source of energy for endogenous mitochondria should counteract the NADH depletion. Corbisier et al. discovered that a readily metabolized energy source, namely D(-)-β-hydroxybutyrate sodium salt, inhibited cell degeneration resulting from the presence of uncoupled mitochondria in a dose dependent manner.

SUMMARY OF THE INVENTION

It is an object of the invention to provide a stable, dermal form of NADH and/or NADPH which can be applied topically to the skin for absorption by the skin.

It is a further object of the invention to provide NADH and/or NADPH compositions which can be applied topically to stimulate the energy production of skin cells.

It is yet a further object of the invention to provide NADH and/or NADPH compositions which can be applied to the skin to increase water uptake by the skin and reduce wrinkle formation.

It is still a further object of the invention to provide NADH and/or NADPH compositions which can be applied to the skin to prolong the life of skin cells.

It is another object of the invention to administer NADH and/or NADPH nasally, sublingually and rectally for a variety of known therapeutic effects.

In accordance with the invention, an NADH and/or NADPH composition is provided for topical application to the skin. It was surprising and totally unexpected to discover that NADH and NADPH are absorbed by the skin and penetrate the cutis to be taken up by the skin cells, where they stimulate certain enzymes which are essential for the energy production of the cells. The enzymes stimulated are principally the mitochondrial enzymes. The NADH and/or NADPH can be incorporated into a skin compatible cream, lotion or cosmetic, or can be combined with micelles of lipophilic substances. Liposomes are preferred vesicles for delivering the greatest dosages of NADH and/or NADPH into the skin.

In other embodiments of the invention, NADH and/or NADPH is administered: intranasally (e.g., as a liquid spray or a powder spray through the nostrils and into the nasal passages to be absorbed by the mucosa), sublingually (e.g., in the form of uncoated tablets inserted underneath the tongue for absorption by the mucosa) and rectally (e.g., in the form of suppositories inserted up the rectum) for known therapeutic effects (e.g., the treatment of Parkinson's disease).

DETAILED DESCRIPTION OF THE INVENTION

In accordance with the first embodiment of the invention, nicotinamide adenine dinucleotide in its reduced form ("NADH") and/or nicotinamide adenine phosphate dinucleotide in its reduced form ("NADPH") are applied to the skin. In describing the invention hereinafter, only NADH shall be referred to as a shorthand, however, it should be appreciated that either NADH or NADPH, or a combination of both, can be used for all applications described herein. The NADH may be delivered to the skin as part of a cream, a lotion, an unguent or salve, an ointment, etc. The NADH may be added to conventional cream or lotion formulations which are skin compatible. The NADH may also be combined with micelles of lipophilic substances, such as phospholipids (e.g., phosphatidylserine). However, the preferred vehicle for delivering NADH to the skin is a liposome. Liposomes have been shown to penetrate the skin more rapidly and extensively than conventional creams. Greater amounts of NADH may be delivered to the skin cells using liposomes.

As known in the art, liposomes are lipid vesicles, the size of which can be selected depending upon how they are prepared. The NADH is entrapped into the liposomes prior to being applied to the skin. The NADH can be entrapped in the liposomes without forming any chemical bonds. The liposomes will then release their NADH content as soon as they have penetrated the membranes of the skin cells because the lipid bilayer which comprises each liposome will degrade. Thus, the liposomes function as a carrier for the NADH to the skin. Another advantage of using liposomes is that the active agent (i.e., the NADH) is protected until it reaches the site where it is to take action (i.e., in the skin cells).

The incorporation of active agents into liposomes for delivery to cells is well known in the art. For example, liposomes have been used to entrap anti-tumor agents, anti-microbial drugs, and anti-inflammatory medication for carrying these agents to the cells. As known in the art, most liposomes are composed of natural or synthetic phospholipids (e.g., lecithins) so that they can be metabolized in the body. Of course, the substances which comprise the liposomes should be non-toxic and non-antigenic. As known in the art, the distribution of the active agent to be delivered by the liposomes in the body (in this case the NADH) can be controlled by adjusting the lipid composition, size, charge, permeability and surface ligands of the liposomes.

As known in the art, liposomes are prepared by removing detergent from equilibrated solutions of mixed lipid and detergent micelles. Natural or synthetic phospholipids, which can be neutral, negatively charged or positively charged, can be used as the lipids. Tetraetherlipids and other bilayer-forming compounds may also be used. Typical lipid compositions of liposomes which can be used in the present invention are egg yolk lecithin and mixtures of egg yolk lecithin with: cholesterol, phosphatidylethanolamine, phosphatidylinositol, phosphatidic acid, stearylamine and cerebroside. When the egg yolk lecithin is used as part of a lipid mixture, the molar ratio of egg yolk lecithin to the other component of the mixture is typically about 3.5:1, however, molar ratios may vary. Other typical lipid compositions which can be used include mixtures of dipalmitoyl phosphatidylcholine with either dimyristoyl phosphatidic acid or dicetylphosphate with the molar ratio of dipalmitoyl phosphatidylcholine to the other component being about 9:1. Other common lipid compositions which can be used are mixtures of distearoyl phosphatidylcholine with dicetylphosphate or with both dicetylphosphate and cholesterol. Hydrogenated soya lecithin in a mixture with dimyristoyl phosphatidic acid (molar ratio 9:1) is yet another common lipid composition for a liposome which can be used.

The detergents used in liposome preparation are mild, and are chosen so that they would not hydrolyze or peroxidize the liposome components. Common detergents known in the art for this purpose are sodium cholate, n-octyl-β-D-glucopyranoside and n-octyl-tetraoxyethylene. Other detergents which can be used are sodium salts of glycocholic acid, deoxycholic acid, taurocholic acid, chenoxycholic acid, n-hexyl- and n-heptyl-glucopyranoside and lauryldimethylaminoxide. The molar ratio of total lipids to total detergents typically ranges from 0.2:1 to 1.15:1. In the case of egg yolk lecithin and sodium cholate, a typical preferred lipid to detergent molar ratio is 0.6:1. In order to achieve these ratios, the lipid concentration in the lipid/detergent micelle solution is typically between 10 and 20 mg/ml, preferably between 10 and 13 mg/ml.

The detergent may be dissolved in the lipid using an organic solvent such as ethanol. The lipid, detergent and solvent are then applied as a thin film onto a rotary evaporator, where they are exposed to aqueous solvents (i.e., water). Upon exposure, the lipid and detergent micelles are formed after several minutes.

The NADH may be entrapped in the liposomes in either of two ways. The NADH may be dissolved in the organic solvent together with the lipid(s) and the detergent(s) during the liposome formation. By this procedure, the NADH will be present in the lipid film before the film is solubilized. Alternatively, the NADH may be entrapped by dissolving it in the aqueous solvent (preferably buffered) before the lipid film is exposed to the aqueous solvent. It is important that the aqueous solution of NADH not have a pH below 7 as NADH (and NADPH) are very unstable at pHs below 7. This second method of entrapment (i.e., dissolving NADH in aqueous solution) is preferred.

The final step in preparing the liposomes is the removal of the detergent. As known in the art, this is generally accomplished by dialysis. An apparatus available from Dianorm GmbH known as the liposomat™ may be used for this purpose. The dialysis should be performed at a constant temperature which is above the transition temperature of the lipid mixture. The liposomes are formed by continuously and rapidly removing the detergent from the lipid/detergent micelles. Suitable dialysis membranes for removing the detergent which can be used in the liposomat™ device are also available from Dianorm. These dialysis membranes are characterized by excellent uniformity of thickness, elasticity and permeability. In the liposomat™, the lipid/detergent micelle solution is suctioned through the dialysis membrane using pumps, whereupon the detergent is removed and the liposomes are formed. As known in the art, several cycles through the dialysis membrane will be necessary to get the detergent concentration down to about 3%, and many cycles will be necessary to result in detergent-free liposomes. In order to reduce the time required to produce detergent-free liposomes, an apparatus known as the liposomat-II™, available from Dianorm, may also be used.

As known in the art, the size of the liposomes can be adjusted by varying the following parameters: rate of dialysis, detergent type, lipid type, lipid/detergent molar ratio, lipid concentration, electrolyte content and pH. Generally, liposome diameter increases with slower rates of dialysis. In general, liposome diameters of 30 nm to 100 nm may be used for effectively encapsulating and delivering NADH to the skin in accordance with the present invention.

The NADH encapsulated by the liposomes is simply applied topically to the skin, and is rubbed into the skin to ensure penetration. Surprisingly, experiments using radiolabelled NADH (and NADPH) have revealed that the NADH (and NADPH) crosses the cutis and enters the cells which comprise the skin proliferation layer. Even NADH (and NADPH) which is not encapsulated by liposomes enters the cells of the proliferation layer, however, greater amounts of the NADH are delivered using the liposomes. Surprisingly, other experiments have also shown that the NADH (and NADPH) goes to the mitochondria where it stimulates the energy production of the cell. The benefits of such stimulated energy production include a prolonged cell life and an increased water uptake by the cell, thereby reducing wrinkle formation.

As discussed above, although the NADH is preferably encapsulated in a liposome prior to application to the skin, this is not essential to obtain beneficial results. The NADH may also be incorporated into a conventional skin compatible cream, lotion or unguent. It is important that the pH of the cream or lotion not be below 7 in order to ensure the stability of the NADH. Preferably, the pH is adjusted to from 8 to 10. Examples of suitable cream formulations are (where %=% by weight):

| NADH Cream | | NADPH Cream | |
| --- | --- | --- | --- |
| NADH | 2% | NADPH | 1% |
| Tocopherol (Vitamin E) | 2% | Tocopherol (Vitamin E) | 2% |
| Panthenol | 1% | Panthenol | 2% |
| Sodium ascorbate | 2% | Sodium ascorbate | 3% |
| Glyceryl stearate | 5% | Cremophor WO 7 | 6% |
| Cetearyl Alcohol | 2% | Vaseline | 30% |
| Isopropyl palmitate | 2% | Isopropyl myristate | 10% |
| Isopropyl myristate | 6% | Lunacera MWN | 6% |
| Petrolatum | 20% | Calcium stearate | 1% |
| Polyethylene glycol 8 (PEG-8) | 2% | Glycerol | 3% |
| Phenoxyethanol | 0.2% | Phenoxyethanol | 0.2% |
| Water | 45.8% | Water | 35.8% |

Examples of lotion formulations are:

| NADH Lotion | | NADPH Lotion | |
| --- | --- | --- | --- |
| NADH | 2% | NADPH | 1% |
| Tocopherol (Vitamin E) | 2% | Tocopherol (Vitamin E) | 2% |
| Panthenol | 1% | Panthenol | 2% |
| Sodiumascorbate | 2% | Sodiumascorbate | 3% |
| Arlatone 985 | 4% | Hostaphat KL 340 N | 3% |
| Atlas G 70147 | 2% | Isopropylpalmiate | 5% |
| Perhydrosqualen | 1% | Paraffine oil | 10% |
| Avocado oil | 1% | Hostacerin PN 73 | 0.6% |
| Paraffine oil | 5% | Triethanolamin | 1.4% |
| Propylenglycol | 3.8% | Propylene glycol | 3.8% |
| Phenoxyethanol | 0.2% | Phenoxyethanol | 0.2% |
| Water | 76% | Water | 68% |

In other embodiments of the invention, the NADH may be administered in other ways for other therapeutic effects. My U.S. Pat. No. 5,332,727 is directed to a stable, ingestable and intestine-absorbable NADH composition which can be taken orally for known therapeutic effects, such as the treatment of Parkinson's disease, Alzheimer's disease and mental depression. The specification of my U.S. Pat. No. 5,332,727 is incorporated herein by reference. The NADH compositions taught by U.S. Pat. No. 5,332,727 are designed to be taken orally.

However, I have now discovered that NADH and/or NADPH is also effective when administered topically (as described above for prolonging the life of skin cells and reducing wrinkles), sublingually, rectally and nasally. The nasal application is particularly effective in the treatment of Alzheimer's disease and Parkinson's disease because the NADH travels directly to the brain, circumventing the blood-brain barrier. Therefore, the nasal administration of NADH provides very fast results.

For nasal administration, the NADH may be taken in the form of a liquid spray or a powder spray, a gel, an ointment, an infusion, an injection or nose drops. Examples of liquid spray formulations are:

| NADH Liquid Spray Formulation | NADPH Liquid Spray Formulation |
| --- | --- |
| NADH 12 mg and Sodium ascorbate 36 mg, dissolved in 1 ml deionized water 1 Spray dose is 0.13 ml containing 1.5 mg NADH | NADPH 2.5 mg and Sodium ascorbate 36 mg, dissolved in 1 ml deionized water 1 Spray dose is 0.13 ml containing 0.32 mg NADPH |

For a powder spray, the NADH is simply ground into a fine powder and atomized from a spray bottle. Preferably, pure NADH is used for the powder spray, however, it can be used in conjunction with a filler, such as mannitol, as described below. The NADH which is inhaled through the nasal passages is absorbed by the mucosa of the nose and travels to the brain through the olfactory neural pathway. NADH administered in this manner has the same therapeutic effects as the oral form as described in U.S. Pat. No. 5,332,727.

Thus, in accordance with the invention, the NADH may be administered to the nasal cavity of a patient afflicted with Parkinson's disease, Alzheimer's disease or mental depression. The NADH may be applied alone or in combination with other substances, for example, a pharmaceutically acceptable carrier or an agent that facilitates the transfer of the NADH through the nasal mucosa. The NADH is administered intranasally as a powder, spray, gel, ointment, infusion, injection or nose drops. The NADH is delivered to the nasal cavity. It is preferred that the NADH be delivered to the olfactory area in the upper third of the nasal cavity, and particularly to the olfactory neuroepithelium in order to promote transport of the NADH into the peripheral olfactory neurons rather than the capillaries within the respiratory epithelium. It is preferred that the transport of NADH to the brain be by means of the nervous system rather than the circulatory system so that the blood-brain barrier from the bloodstream into the brain is circumvented. However, good results can also be obtained through the bloodstream.

Surprisingly, it has been discovered that NADH (and NADPH) is capable of at least partially dissolving in the fluids that are secreted by the mucous membrane which surrounds the cilia of the olfactory receptor cells of the olfactory epithelium so that it may be absorbed into the olfactory neurons. The NADH may be combined with a carrier or other substance that fosters dissolution within nasal secretions, such as the ganglioside GM-1 or the phospolipid phosphatidylserine, or emulsifiers such as polysorbate 80. The NADH may be combined with micelles comprised of lipophilic substances which modify the permeability of the nasal membrane to enhance absorption of the NADH. Lipophilic micelles which are effective for this purpose include the gangliosides, the phospholipids and phosphatidylserine. Alternatively, the NADH may be combined with liposomes to enhance absorption of the NADH into the olfactory system.

I have also discovered that NADH (and/or NADPH) is effective when administered sublingually. Like nasal administration, sublingual resorption of NADH achieves very fast results. The NADH is merely placed underneath the tongue and resorbed. Unlike the oral form of NADH described in U.S. Pat. No. 5,332,727, a sublingual form should not be coated with an acid stable protective coating.

It has also been discovered that good results are obtained when NADH is administered rectally. However, results are not obtained as quickly as in the case of nasal or sublingual administration. NADH may be administered rectally in the form of suppositories. A suitable suppository formulations are:

| NADH Suppository Formulation | | NADPH Suppository Formulation | |
|---|---|---|---|
| NADH | 5 mg | NADPH | 2 mg |
| Sodium ascorbate | 20 mg | Sodium ascorbate | 20 mg |
| Suppository mass | 2475 mg | Suppository mass | 2478 mg |
| (Massa Novata BC, Henkel Inc) | | (Maasa Novata BC, Henkel Inc) | |

Although NADH and/or NADPH may be used by themselves in pure form (they are quite stable in compressed form when protected from light), it is preferred that they be combined in a galenic formulation with a stabilizer, and most preferably with both a stabilizer and a filler. The use of a stabilizer is preferred to prevent oxidation of NADH and NADPH to $NAD^+$ and $NADP^+$, respectively. Although NADH and NADPH are active for the variety of therapeutic effects discussed above, $NAD^+$ and $NADP^+$ are ineffective. Therefore, oxidation of NADH and NADPH must be prevented during storage to provide for a reasonable shelf life. It has been found that the following stabilizers are effective and result in the greatest shelf stability for NADH and NADPH: $NaHCO_3$; ascorbic acid and sodium ascorbate; tocopherols and tocopherolacetates; polyvinylpyrolidone ("PVP") 12 (12 representing the molecular weight 12,000); PVP 25; PVP 40; PVP PF 17 (meaning polymer having a molecular weight from 17,000) and PVP PF 60. NADH/NADPH formulations containing such stabilizers are stable for up to two years. Other various stabilizers will become apparent to those skilled in the art.

Suitable fillers for use with NADH and NADPH include: mannitol, microcrystalline cellulose, carboxymethyl cellulose; and dibasic calcium phosphate. Other suitable fillers will become apparent to those skilled in the art. Lactose should be avoided as a filler because it reacts with NADH.

In general, a preferred formulation will include about 3 to 10% by weight NADH and/or NADPH; about 1 to 10% by weight stabilizer; and the remainder as filler. Such a formulation, after being compressed into a pill and coated, is stable for over 24 months.

The NADH and/or NADPH, together with the optional stabilizer and filler, may be formed into tablets, capsules, microtablets or micropellets by processes known in the art of pill manufacturing. Tablets may be formed either by direct compression or by granulation followed by compression. Capsules may be formed by blending the components and subsequently filling capsules with the blend using conventional automatic filling equipment. Microtablets may be formed by compressing powdered or granulated components into, e.g., 2 mm diameter tablets.

In the case of direct compression into tablets, a particularly preferred formulation is: NADH 5%, sodium ascorbate 5%, magnesium stearate 3%, talc 4%, silicon dioxide 1%, and mannitol 82%.

In the case of capsules, a particularly preferred formulation is: NADH 5%, sodium ascorbate 5%, polyvinylpyrolidone (PVP) 5%, microcrystalline cellulose 77%, magnesium stearate 3%, alpha-tocopherolacetate 1%, talc 3%, and silicon dioxide 1%.

A suitable single dose of NADH and/or NADPH for sublingual, rectal or nasal application is 5 to 500 mg, preferably 25 to 100 mg. A suitable daily dose is 5 to 1,500 mg, preferably 25 to 300 mg. Such dosages improve the motor system in Parkinsonian patients.

Physiologically acceptable salts of the coenzymes NADH and NADPH may also be used in all embodiments of the present invention (i.e., nasal, sublingual, rectal and dermal forms) Acceptable salts of NADH/NADPH include all known physiologically acceptable acidic and basic salt-forming substances, for example: inorganic acids such as, for example, hydrohalic acids, sulfuric acid, phosphoric acid; organic acids such as, for example, aliphatic or aromatic carboxylic acids, e.g., formic acid, acetic acid, succinic acid, lactic acid, malic acid, tartaric acid, citric acid, maleic acid, phenylacetic acid, benzoic acid, salicylic acid or ascorbic acid; or alkali metal hydroxides or alkaline earth metal hydroxides or salts.

NADH, NADPH or their physiologically compatible salts can be manufactured in the usual manner with pharmaceutically acceptable auxiliaries and carrier materials. If necessary, they can also be used in combination with other active ingredients, for example, postsynaptic dopamine agonists such as Lisuride or Amorphine.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are accordingly to be regarded in an illustrative rather than a restrictive sense.

What is claimed is:

1. A method of treating Parkinson's disease, Alzheimer's disease or mental depression comprising the step of administering NADH or NADPH, or a physiologically acceptable salt thereof, to the rectum of a person afflicted with Parkinson's disease, Alzheimer's disease or mental depression.

2. The method according to claim 1 wherein the NADH or NADPH, or salt thereof, is administered to the rectum in the form of a suppository.

3. A method of treating Alzheimer's disease, Parkinson's disease or mental depression comprising the step of administering NADH or NADPH, or a physiologically acceptable salt thereof, to the olfactory neuroepithelium of a nasal passage of a person afflicted with Alzheimer's disease, Parkinson's disease or mental depression to result in absorption of the NADH or NADPH, or salt thereof, into the mucosa of the nose and directly into the olfactory neurons.

4. The method according to claim 3 wherein the NADH or NADPH, or salt thereof, is administered in the form of an atomized powder.

5. The method according to claim 4 wherein the NADH or NADPH, or salt thereof, is administered in the form of a liquid spray.

6. The method according to claim 3, wherein the NADH or NADPH is stabilized with a stabilizer which is effective to inhibit oxidation of NADH or NADPH to $NAD^+$ or $NADP^+$, respectively.

7. The method according to claim 1, wherein the NADH or NADPH is stabilized with a stabilizer which is effective to inhibit oxidation of NADH or NADPH to $NAD^+$ or $NADP^+$, respectively.

* * * * *